US012797632B2

(12) United States Patent
Doyle

(10) Patent No.: US 12,797,632 B2
(45) Date of Patent: Nov. 17, 2026

(54) PHOTOBIOMODULATION THERAPY DEVICE

(71) Applicant: Patrick Doyle, Reno, NV (US)

(72) Inventor: Patrick Doyle, Reno, NV (US)

(*) Notice: Subject to any disclaimer, the term of this patent is extended or adjusted under 35 U.S.C. 154(b) by 165 days.

(21) Appl. No.: 18/777,766

(22) Filed: Jul. 19, 2024

(65) Prior Publication Data

US 2026/0021320 A1 Jan. 22, 2026

(51) Int. Cl.
*A61N 5/06* (2006.01)

(52) U.S. Cl.
CPC .... *A61N 5/0613* (2013.01); *A61N 2005/0629* (2013.01); *A61N 2005/0632* (2013.01); *A61N 2005/0645* (2013.01); *A61N 2005/0652* (2013.01); *A61N 2005/0659* (2013.01); *A61N 2005/0663* (2013.01)

(58) Field of Classification Search
CPC .... A61N 2005/0645; A61N 2005/6052; A61N 2005/0659; A61N 2005/0663; A61N 2005/0626; A61N 2005/0633; A61N 2005/0642
See application file for complete search history.

(56) References Cited

U.S. PATENT DOCUMENTS

| | | | | | |
|---|---|---|---|---|---|
| 5,358,503 | A * | 10/1994 | Bertwell | A61N 5/0616 606/2 |
| 6,860,896 | B2 * | 3/2005 | Leber | A61N 5/0619 128/898 |
| 2018/0360665 | A1 * | 12/2018 | Melone | A61N 5/0613 |
| 2021/0001141 | A1 * | 1/2021 | Pfiffner | A61N 5/06 |
| 2022/0133518 | A1 * | 5/2022 | Coggins | A61F 5/0127 602/27 |
| 2024/0091551 | A1 * | 3/2024 | Cabana | A61N 5/067 |
| 2024/0359029 | A1 * | 10/2024 | Kerns | A61N 5/0613 |

* cited by examiner

*Primary Examiner* — Brian T Gedeon
(74) *Attorney, Agent, or Firm* — The Rapacke Law Group, P.A.; Andrew S. Rapacke; Kenneth F. Brooks

(57) ABSTRACT

A photobiomodulation therapy device can include a receiving pad for receiving a portion of a user's body; a first plurality of blue LEDs, wherein at least a first portion of the first plurality of blue LEDs is attached to the receiving pad; a second plurality of red LEDs, wherein at least a first portion of the second plurality of red LEDs is attached to the receiving pad; and a third plurality of infrared LEDs, wherein at least a first portion of the third plurality of infrared LEDs is attached to the receiving pad; control circuitry operably coupled to the first plurality of blue LEDs, the second plurality of red LEDs, and the third plurality of infrared LEDs, wherein the control circuitry is configured at least to: set the pulse rates of the first plurality of blue LEDs, the second plurality of red LEDs, and the third plurality of infrared LEDs.

10 Claims, 4 Drawing Sheets

PHOTOBIOMODULATION THERAPY DEVICE

TECHNICAL FIELD

Embodiments disclosed herein can relate to photobiomodulation therapy devices.

BACKGROUND

Photobiomodulation therapy devices emit blue, red, infrared light to release nitric oxide from hemoglobin in a user's body so that the nitric oxide can enter endothelial cells and relax blood vessels. Such devices may have blue, red and infrared light emitting diodes (LEDs) with fixed pulse frequencies. As the tissue penetration depth of light increases with its wavelength, blue light from blue LEDs may have a smaller tissue penetration depth than red light from red LEDs, and red light from red LEDs may have a smaller tissue penetration depth than infrared light from infrared LEDs.

The following non-patent literature references relate to the present disclosure and are hereby incorporated by reference herein:

[1] C. Opländer, et al., Mechanism and biological relevance of blue-light (420-453 nm)-induced nonenzymatic nitric oxide generation from photolabile nitric oxide derivates in human skin in vitro and in vivo, Free Radical Biology and Medicine, 2013.

[2] C. Ash, et al., Effect of wavelength and beam width on penetration in light-tissue interaction using computational methods, Lasers In Medical Science, 2017.

[3] A. B. Kochman, Monochromatic Infrared Photo Energy and Physical Therapy for Peripheral Neuropathy: Influence on Sensation, Balance, and Falls, Journal of Geriatric Physical Therapy, 2004.

[4] A. C. Barolet, et al., Light-induced nitric oxide release in the skin beyond UVA and blue light: Red & near-infrared wavelengths, Nitric Oxide, 2021.

[5] W. M. Flerx, et al., A Combined Treatment Protocol for Patients With Diabetic Peripheral Neuropathy, Federal Practitioner, 2015.

[6] L. R. Horwitz, et al., Augmentation of Wound Healing Using Monochromatic Infrared Energy, Advances in Wound Care, 1999.

[7] Horwitz L, Burke T J, Carnegie D E. Augmentation of Wound Healing Using Monochromatic Infrared Energy. Advances in Wound Care. 1999; 12:35-40.

[8] Noble J G, Lowe A S, Baxter G D. Monochromatic Infrared Irradiation (890): Effect of a Multisource Array upon Conduction in the Human Median Nerve. Journal of Clinical Laser Medicine and Surgery. 2001; 19:291-295.

[9] Kochman A B, Carnegie D E, Burke T J. Symptomatic Reversal of Peripheral Neuropathy in Patients with Diabetes. Journal of the American Podiatric Medical Association. 2002; 92:125-130.

[10] Prendergast J J, Miranda G, Sanchez M. Improvement of Sensory Impairment in Patients with Peripheral Neuropathy. Endocrine Practice. 2004; 10:24-30.

[11] Leonard D R, Farooqi M H, Myers S. Restoration of Sensation, Reduced Pain, and Improved Balance in Subjects with Diabetic Peripheral Neuropathy; A Randomized, Double Blind, Placebo Controlled Study. Diabetes Care. 2004; 27:168-172.

[12] Kochman A B. Monochromatic Infrared Photo Energy and Physical Therapy for Peripheral Neuropathy: Influence on Sensation, Balance and Falls. Journal of Geriatric Physical Therapy. 2004; 27:16-19.

[13] Powell M W, Carnegie D E, Burke T J. Reversal of Diabetic Peripheral Neuropathy and New Wound Incidence: The Role of MIRE. Advances in Skin & Wound Care. 2004; 17(6): 295-300.

[14] DeLellis S, Carnegie D E, Burke T J. Improved Sensitivity in Patients with Peripheral Neuropathy: Effects of Monochromatic Infrared Photo Energy. Journal of the American Podiatric Medical Association. 2005; 95(2): 143-147.

[15] Harkless L, DeLellis S, Burke T J. Improved Foot Sensitivity and Pain Reduction in Patients with Peripheral Neuropathy after Treatment with Monochromatic Infrared Photo Energy-MIRE™. Journal of Diabetes and Its Complications. 2006; 20(2): 81-87.

[16] Volkert W, Hassan A, Hassan M, et al. Effectiveness of Monochromatic Infrared Photo Energy and Physical Therapy for Peripheral Neuropathy: Changes in Sensation, Pain and Balance—A Multi-Center Chart Review. Physical and Occupational Therapy in Geriatrics. 2006; 24(2): 7-18.

[17] Powell M W, Carnegie D H, Burke T J. Reversal of Diabetic Peripheral Neuropathy with Photo Therapy (MIRE™) Decreases Falls and the Fear of Falling, and Improves Activities of Daily Living in Seniors. Age and Ageing. 2006; 35(1): 11-16.

[18] Burke T J. Infrared Photo Energy May Reduce Neuropathic Pain. Practical Pain Management. 2007; 7(6): 57-63.

[19] Nather A, Sim Y E, Chew L L, Neo S H. Anodyne Therapy for Recalcitrant Diabetic Foot Ulcers: A Report of Four Cases. Journal of Orthopaedic Surgery. 2007; 15(3): 361-4.

[20] Mitchell, U. Use of Near Infrared Light to Reduce Symptoms Associated with Restless Leg Syndrome in a Woman: a Case Report. J Med Case Reports. 2010; 4:286.

[21] Mitchell, U, Myrer J W, Johnson A W, Hilton S C. Restless Legs Syndrome and Near Infrared Light: An Alternative Treatment Option. Physiotherapy Theory and Practice. 2010 Oct. 26.

[22] Mak, M, Cheing, G. Immediate Effects of Monochromatic Infrared Energy on Microcirculation in Healthy Subjects. Photomedicine and Laser Surgery. 2012; 30(2): 1-8.

[23] Hsieh, R, Liao, W, Lee, W. Local and Systemic Cardiovascular Effects from Monochromatic Infrared Therapy in Patients with Knee Osteoarthritis: A Double-Blind, Randomized, Placebo-Controlled Study. Evidence-Based Complementary and Alternative Medicine. 2012; Article ID 583016.

[24] Ammar, T. Monochromatic Infrared Photo Energy in Diabetic Peripheral Neuropathy. International Scholarly Research Network (ISRN) Rehabilitation. 2012; Article ID 484307.

[25] Ahmed, E, Maayah, M, Mohammad Abu Asi, Y. Anodyne Therapy Versus Exercise Therapy in Improving the Healing Rates of Venous Leg Ulcer. International Journal of Research in Medical Sciences. 2013; August; 1(3): 198-203.

[26] Ru-Lan Hsieh; Wen-Chung Lee. Short-term Therapeutic Effects of 890-Nanometer Light Therapy for Chronic LowBack Pain: A Double-Blind Randomized Placebo-Controlled Study. Lasers in Medical Science. 2013 Jul. 3.

[27] Tarek Abdel Rahman Ali Ammar. Monochromatic Infrared Photo Energy versus Low Level Laser Therapy in patients with Knee Osteoarthitis. J Lasers Med Sci 2014; 5(4): 176-82.

[28] He Y, Yip S L, Cheung K K, Huang L, Wang S, Cheing G L. The effect of monochromatic infrared energy on diabetic wound healing. Int Wound J. 2013 December; 10(6): 645-52. doi: 10.1111/j.1742-481X.2012.01039.x. Epub 2012 Jul. 9.

There is a need for a photobiomodulation therapy device that includes red, infrared, and blue LEDs with varying pulse frequencies to increase the amount of nitric oxide released from hemoglobin in a user's body.

SUMMARY

This summary is provided to introduce a variety of concepts and/or aspects in a simplified form that is further disclosed in the detailed description, below. This summary is not intended to identify key or essential inventive concepts of the claimed subject matter, nor is it intended for determining the scope of the claimed subject matter.

A photobiomodulation therapy device can include a receiving pad for receiving a portion of a user's body; a first plurality of blue LEDs, wherein at least a first portion of the first plurality of blue LEDs is attached to the receiving pad; a second plurality of red LEDs, wherein at least a first portion of the second plurality of red LEDs is attached to the receiving pad; and a third plurality of infrared LEDs, wherein at least a first portion of the third plurality of infrared LEDs is attached to the receiving pad; control circuitry operably coupled to the first plurality of blue LEDs, the second plurality of red LEDs, and the third plurality of infrared LEDs, wherein the control circuitry is configured at least to: set the pulse rates of the first plurality of blue LEDs, the second plurality of red LEDs, and the third plurality of infrared LEDs.

BRIEF DESCRIPTION OF THE DRAWINGS

A complete understanding of the present features or aspects and the advantages and features thereof will be more readily understood by reference to the following detailed description when considered in conjunction with the accompanying drawings wherein.

Figure 1:
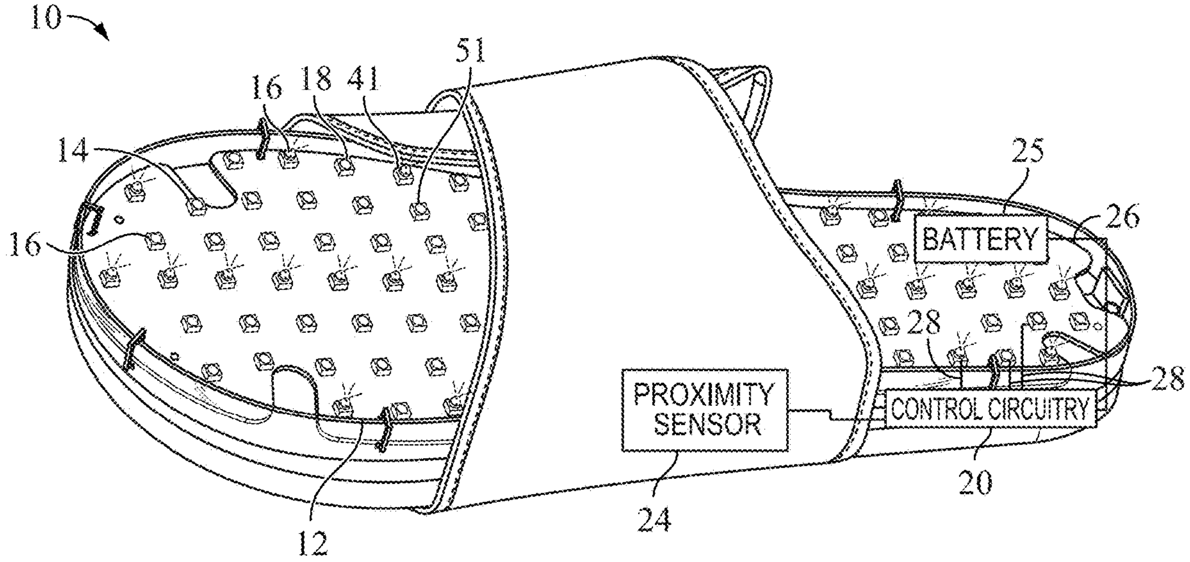
FIG. 1 illustrates a photobiomodulation therapy device, according to some embodiments disclosed herein.

The drawings are not necessarily to scale, and certain features and certain views of the drawings may be shown exaggerated in scale or in schematic in the interest of clarity and conciseness.

DETAILED DESCRIPTION

Any specific details of features or aspects are used for demonstration purposes only, and no unnecessary limitations or inferences are to be understood therefrom.

Before describing in detail exemplary aspects, it is noted that the aspects reside primarily in combinations of components and procedures related to the systems, methods, and media disclosed herein. Accordingly, the systems, methods, and media components and processes have been represented where appropriate by conventional symbols in the drawings, showing only those specific details that are pertinent to understanding the aspects of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship, or order between such entities or elements. Furthermore, there is no intention to be bound by any expressed or implied theory presented in the preceding technical field, background, summary, or the following detailed description. It is also to be understood that the specific devices and processes illustrated in the attached drawings, and described in the following specification, are simply exemplary aspects of the inventive concepts defined in the appended claims. Hence, specific steps, process order, dimensions, component connections, and other physical characteristics relating to the aspects disclosed herein are not to be considered as limiting, unless the claims expressly state otherwise. The use or mention of any single element contemplates a plurality of such element, and the use or mention of a plurality of any element contemplates a single element (for example, "a device" and "devices" and "a plurality of devices" and "one or more devices" and "at least one device" contemplate each other), regardless of whether particular variations are identified and/or described, unless impractical, impossible, or explicitly limited.

Figure 2:
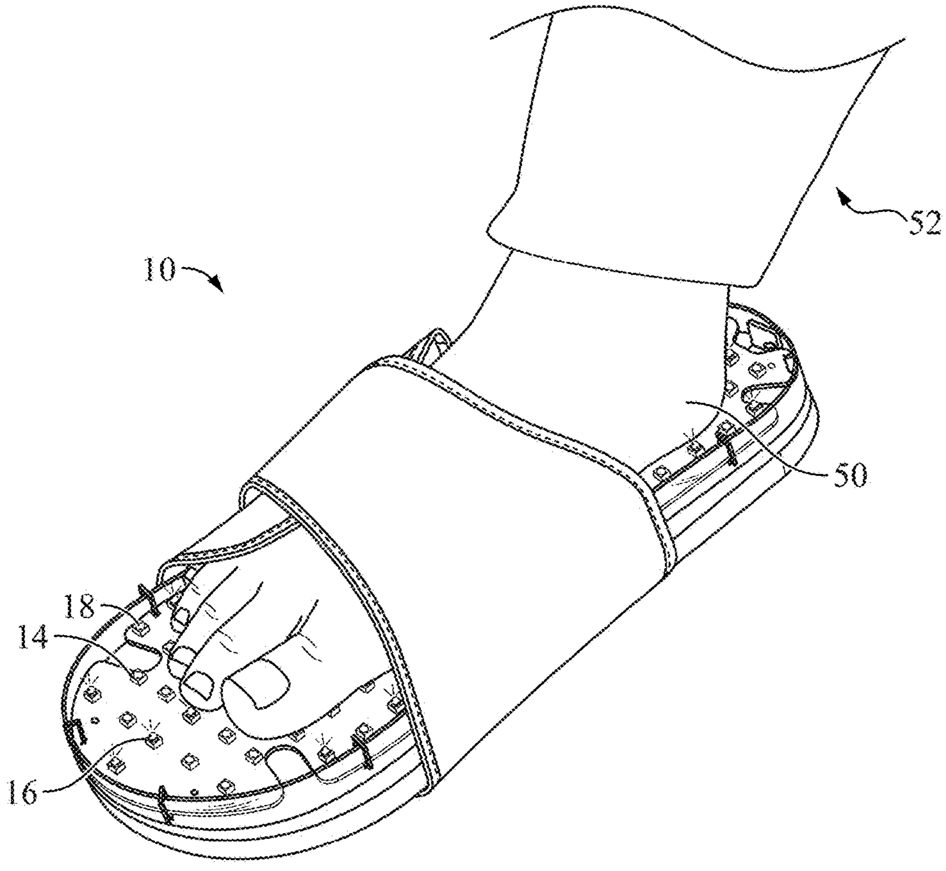
FIG. 2 illustrates a photobiomodulation therapy device worn by a user, according to some embodiments disclosed herein.

Referring to FIG. 1, a photobiomodulation therapy device 10 can include a first receiving pad 12 that is constructed to receive a first portion (e.g., foot 50 in FIG. 2) of a user's body (e.g., 52 in FIG. 2). The photobiomodulation therapy device 10 can include a first plurality of blue light emitting diodes (LEDs) 14, a second plurality of red LEDs 16, a third plurality of infrared LEDs 18, or any combination thereof. The first plurality of blue LEDs 14 can emit light having wavelengths primarily in the range from 461 nm to 477 nm. The second plurality of red LEDs 16 can emit light having wavelengths primarily in the range from 627 nm to 645 nm. The third plurality of infrared LEDs 18 can emit light having wavelengths primarily in the range from 842 nm to 860 nm.

In some embodiments, at least a first portion 31 of the first plurality of blue LEDs 14 is attached to the first receiving pad 12. In some embodiments, at least a first portion 41 of the second plurality of red LEDs 16 is attached to the first receiving pad 12. In some embodiments, at least a first portion 51 of the third plurality of infrared LEDs 18 is attached to the first receiving pad 12.

In some embodiments, at least one proximity sensor 24 can be attached to at least the first receiving pad 12. A portable battery 25 can be constructed and arranged to provide power to the first plurality of blue LEDs 14, the second plurality of red LEDs 16, and the third plurality of infrared LEDs 18. Alternatively or additionally, a power supply 27 can be constructed and arranged to receive power from an external power source (not shown), and provide the power to the first plurality of blue LEDs 14, the second plurality of red LEDs 16, and the third plurality of infrared LEDs 18, and any other components of the photobiomodulation therapy device 10.

Figure 3B:
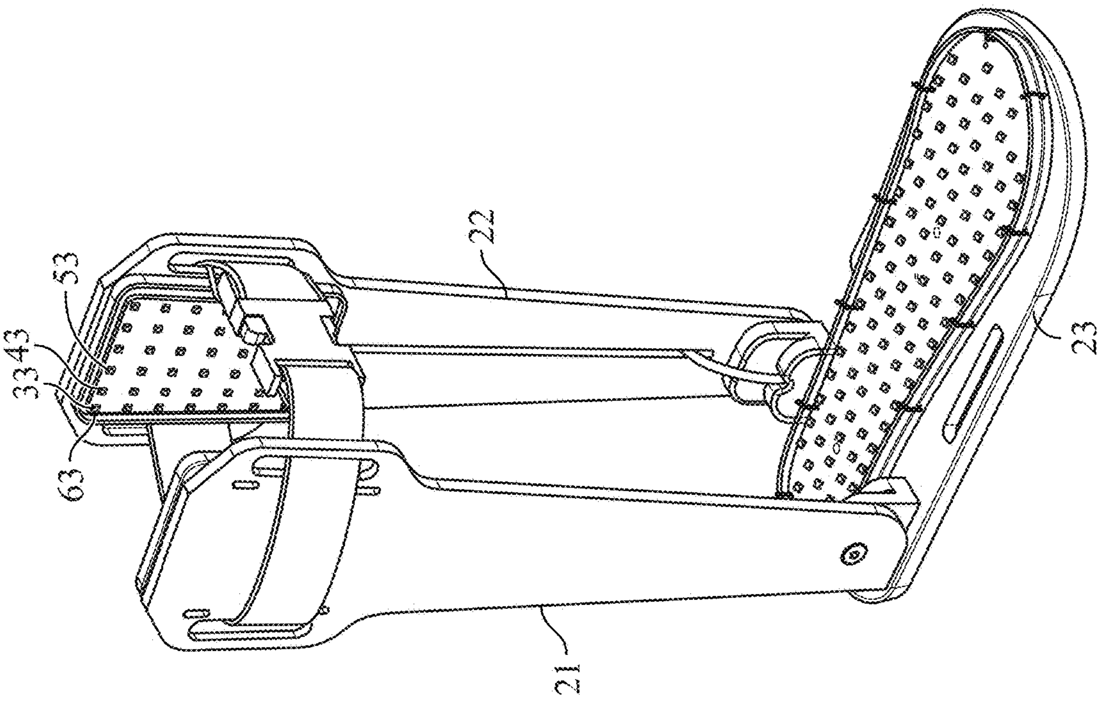
FIG. 3B illustrates the photobiomodulation therapy device of FIG. 3 worn by a user, according to some embodiments disclosed herein.
Figure 3A:
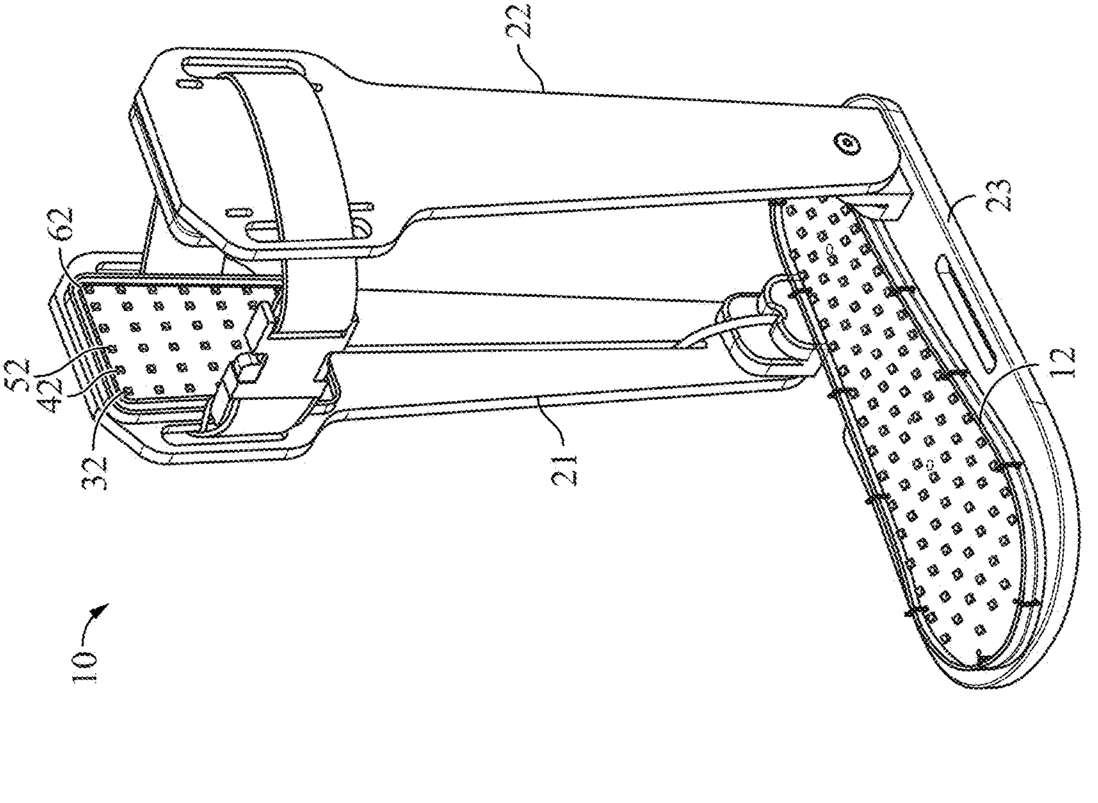
FIG. 3A illustrates a photobiomodulation therapy device with two side arms, according to some embodiments disclosed herein.
Figure 4:
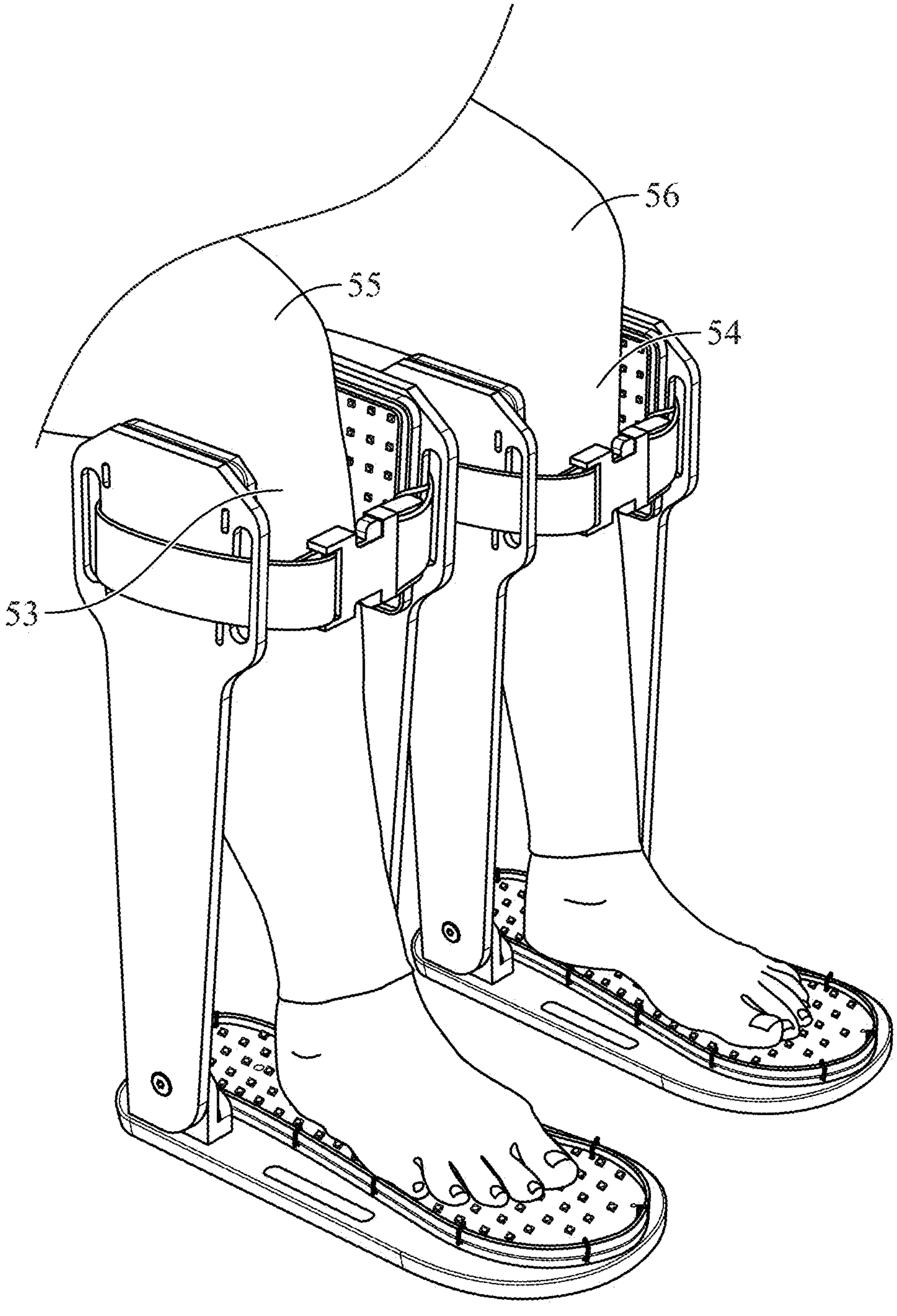
FIG. 4 illustrates two photobiomodulation therapy devices worn by a user, according to some embodiments disclosed herein.

Referring to FIG. 3A, in some embodiments, the photobiomodulation therapy device 10 can include a second receiving pad 62 that is constructed to receive a second portion (e.g., portion 53 of user's leg 55 in FIG. 4) of the user's body 52.

In some embodiments, at least a second portion 32 of the first plurality of blue LEDs 14 is attached to the second receiving pad 62. In some embodiments, at least a second portion 42 of the second plurality of red LEDs 16 is attached to the second receiving pad 62. In some embodiments, at least a second portion 52 of the third plurality of infrared LEDs 18 is attached to the second receiving pad 62.

In some embodiments, the photobiomodulation therapy device 10 can include a base plate 23. In some embodiments, the first receiving pad 12 can be disposed on the base plate 23 and positioned between a first arm 21 and a second arm 22. In some embodiments, the first arm 21 can be pivotally connected to the base plate 23. In some embodiments, the second arm 22 can be pivotally connected to the base plate 23.

In some embodiments, the second receiving pad 62 can be attached to the first arm 21. In some embodiments, the second portion 42 of the second plurality of red LEDs 16 can be attached to the first arm 21. In some embodiments, the second portion 52 of the third plurality of infrared LEDs 18 can be attached to the first arm 21.

Referring to FIG. 3B. in some embodiments, the photobiomodulation therapy device 10 can include a third receiving pad 63 that is constructed to receive a third portion (e.g., portion 54 of user's leg 56 in FIG. 4) of the user's body 52. In some embodiments, at least a third portion 33 of the first plurality of blue LEDs 14 is attached to the third receiving pad 63. In some embodiments, at least a third portion 43 of the second plurality of red LEDs 16 is attached to the third receiving pad 63. In some embodiments, at least a third portion 53 of the third plurality of infrared LEDs 18 is attached to the third receiving pad 63.

In some embodiments, the third receiving pad 63 can be attached to the second arm 22. In some embodiments, the third portion 43 of the second plurality of red LEDs 16 can be attached to the second arm 22. In some embodiments, the third portion 53 of the third plurality of infrared LEDs 18 can be attached to the second arm 22.

Referring back to FIG. 1, in some embodiments, control circuitry 20 can be operably coupled to the first plurality of blue LEDs 14, the second plurality of red LEDs 16, and the third plurality of infrared LEDs 18. In some embodiments, the control circuitry 20 can be configured at least to activate, deactivate, and control a pulse rate of any LED of the first plurality of blue LEDs 14, the second plurality of red LEDs 16, and the third plurality of infrared LEDs 18.

In some embodiments, the control circuitry 20 can be electrically connected to the first plurality of blue LEDs 14, the second plurality of red LEDs 16, and the third plurality of infrared LEDs 18 via electrical connections 28. A power cable 26 can be electrically connected to the battery 25 and to the control circuitry 20 to provide power to the first plurality of blue LEDs 14, the second plurality of red LEDs 16, and the third plurality of infrared LEDs.

Figure 5:
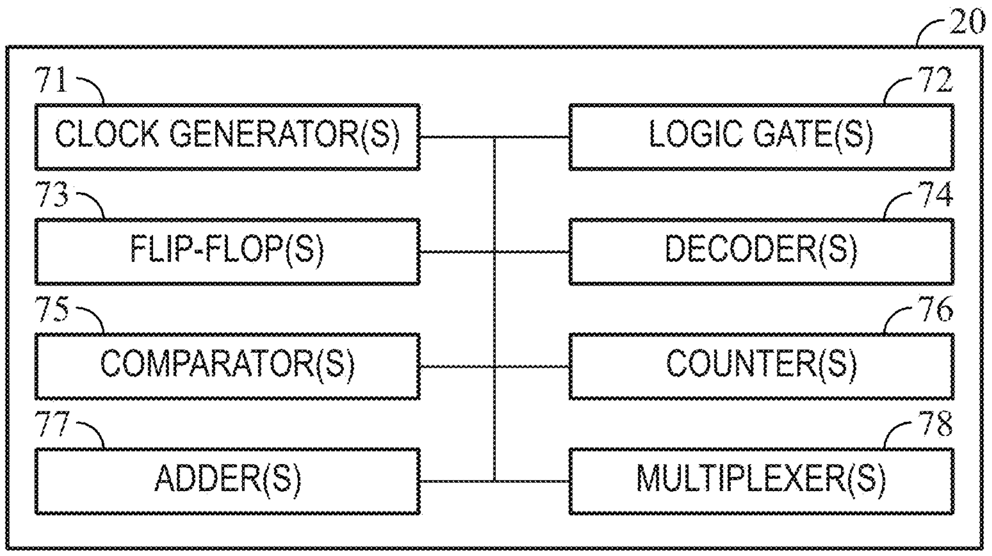
FIG. 5 illustrates a block diagram of components of control circuitry for a photobiomodulation therapy device, according to some embodiments disclosed herein.

Referring to FIG. 5, in some embodiments, the control circuitry 20 can include any suitable digital logic circuitry such as, for example, one or more clock generators 71, one or more logic gates 72, one or more flip-flops 73, one or more decoders 74, one or more comparators 75, one or more counters 76, one or more adders 77, one or more multiplexers 78, any other digital logic circuitry to activate, deactivate, and control a pulse rate of any LED, or any combination thereof. Suitable logic gates can include one or more AND gates, one or more OR gates, one or more NOT gates, one or more NAND gates, one or more NOR gates, one or more XOR gates, or any combination thereof.

Figure 6:
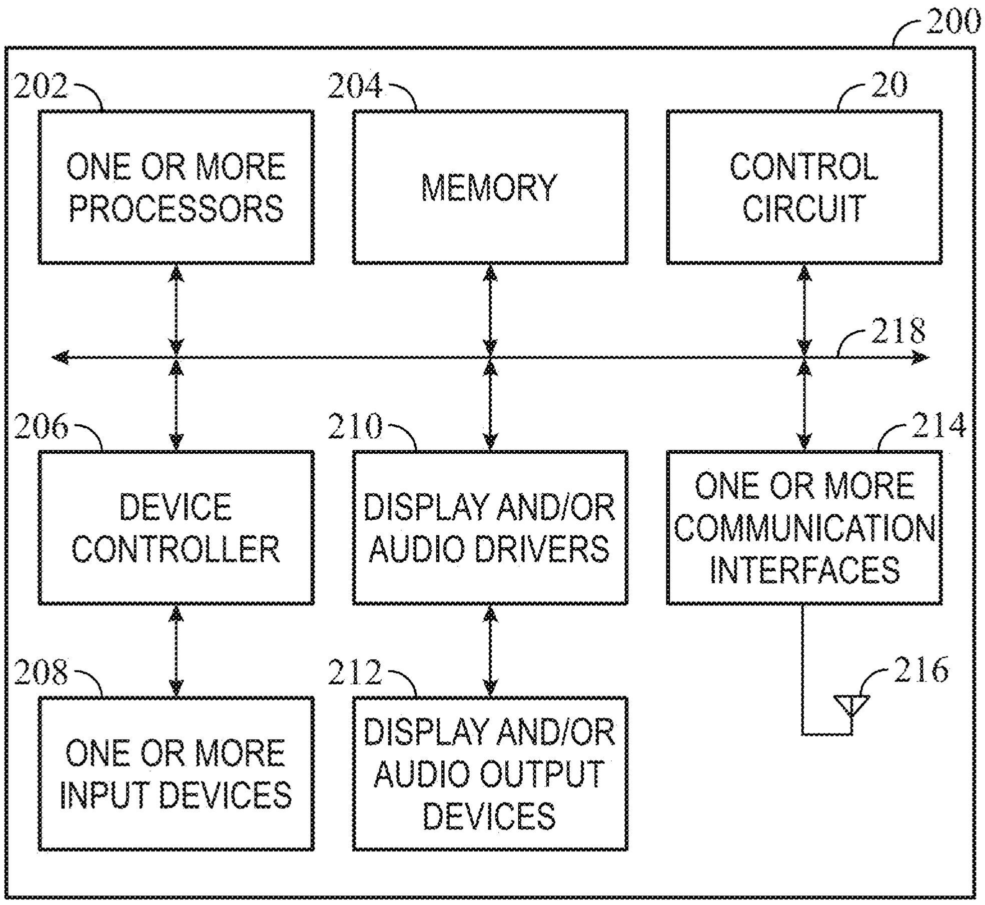
FIG. 6 illustrates a block diagram of hardware of a computing device for a photobiomodulation therapy device, according to some embodiments disclosed herein.

Referring to FIG. 6, the photobiomodulation therapy device 10 can include a computing device 200. In some embodiments, the computing device 200 can include one or more processors 202, memory 204, a device controller 206, one or more input devices 208, display and/or audio drivers 210, display and/or audio output devices 212, one or more communication interfaces 214, one or more antennas 216, a bus 218, or any combination thereof. In some embodiments, the computing device 200 can include the control circuitry 20 in FIG. 5.

In some embodiments, the one or more processors 202 can include any suitable hardware processor, such as a central processing unit (CPU), a graphics processing unit (GPU), a tensor processing unit (TPU), an accelerated processing unit (APU), any other type of processing unit, or any combination thereof. In some embodiments, the one or more processors 202 can include a microprocessor, a microcontroller, a digital signal processor, dedicated logic, an application-specific integrated circuit (ASIC), a field programmable gate array (FPGA), an accelerator (e.g., an artificial intelligence (AI) accelerator or a cryptographic accelerator), any other suitable circuitry for controlling the functioning of a general purpose computer or a special purpose computer, or any combination thereof.

In some embodiments, the memory 204 can include any suitable memory, storage, or a combination thereof for storing programs, data, and/or any other suitable information. For example, memory 204 can include volatile memory, non-volatile memory, or any combination thereof. In some embodiments, memory 204 can include random access memory, read-only memory, flash memory, a hard disk drive, a solid state drive, optical media, any other suitable memory, or any combination thereof.

In some embodiments, the device controller 206 can include any suitable processor or circuitry for controlling and receiving any input from the one or more input devices 208. In some embodiments, the one or more input devices 208 can include a touchscreen, a keyboard, a mouse, one or more buttons, a voice recognition circuit, a camera, one or more sensors, any other suitable input device, or any combination thereof. In some embodiments, the one or more sensors can include one or more accelerometers, one or more gyroscope sensors, one or more microphones, any other suitable sensors (e.g., an optical sensor, a temperature sensor, a near field sensor), or any combination thereof.

In some embodiments, the display and/or audio drivers 210 can include any suitable circuitry for controlling and driving output to one or more display and/or audio output devices 212. For example, the output devices can include a display (e.g., including a touchscreen, a flat-panel display, a cathode ray tube display, a projector, any other suitable display or presentation device, or any combination thereof), one or more speakers, or a combination thereof.

In some embodiments, the one or more communication interfaces 214 can include any suitable circuitry for interfacing with one or more communication networks. For example, the one or more communication interfaces 214 can include network interface card circuitry, wired communication circuitry, wireless communication circuitry, any other suitable communication network circuitry, or any combination thereof.

In some embodiments, the one or more antennas 216 can wirelessly communicate with a communication network. In some embodiments, the one or more antennas 216 can be omitted.

In some embodiments, the bus 218 can include any suitable communication system for communicating data, addresses, control signals, power, or any combination thereof, between two or more components 202, 204, 205, 206, 210, and 214. In some embodiments, the bus 218 can include any suitable conductors that are constructed and arranged to communicate data, addresses, control signals, power, or any combination thereof, between two or more components 202, 204, 205, 206, 210, and 214.

In some embodiments, any other suitable component(s) can be included in the computing device 200.

In some embodiments, the one or more processors 202, the control circuitry 20, or a combination thereof can activate, deactivate, and control a pulse rate of any LED of the first plurality of blue LEDs 14, the second plurality of red LEDs 16, and the third plurality of infrared LEDs 18 in response to receiving sensor data from the at least one proximity sensor 24.

In some embodiments, the one or more processors 202, the control circuitry 20, or a combination thereof can activate the first plurality of blue LEDs 14 so that the first plurality of blue LEDs 14 have a pulse rate of 146 Hz for a predetermined amount of time.

The pulse rate of the first plurality of blue LEDs 14 can then be increased to 219 Hz for a predetermined amount of time.

The pulse rate of the first plurality of blue LEDs 14 can then be increased to 365 Hz for a predetermined amount of time.

The pulse rate of the first plurality of blue LEDs 14 can then be increased to 584 Hz for a predetermined amount of time.

The pulse rate of the first plurality of blue LEDs 14 can then be increased to 946 Hz for a predetermined amount of time.

The first plurality of blue LEDs 14 can then be deactivated so that power is no longer provided to the first plurality of blue LEDs 14.

In some embodiments, the one or more processors 202, the control circuitry 20, or a combination thereof can activate the second plurality of red LEDs 16 and the third plurality of infrared LEDs 18 so that the second plurality of red LEDs 16 and the third plurality of infrared LEDs 18 have a pulse rate of 146 Hz for a predetermined amount of time.

The pulse rate of the second plurality of red LEDs 16 and the third plurality of infrared LEDs 18 can be increased to 219 Hz for a predetermined amount of time.

The pulse rate of the second plurality of red LEDs 16 and the third plurality of infrared LEDs 18 can be increased to 365 Hz for a predetermined amount of time.

The pulse rate of the second plurality of red LEDs 16 and the third plurality of infrared LEDs 18 can be increased to 584 Hz for a predetermined amount of time.

The pulse rate of the second plurality of red LEDs 16 and the third plurality of infrared LEDs 18 can be increased to 946 Hz for a predetermined amount of time.

The pulse rate of the second plurality of red LEDs 16 and the third plurality of infrared LEDs 18 can be increased to 1524 Hz for a predetermined amount of time.

The pulse rate of the second plurality of red LEDs 16 and the third plurality of infrared LEDs 18 can be increased to 2487 Hz for a predetermined amount of time.

The pulse rate of the second plurality of red LEDs 16 and the third plurality of infrared LEDs 18 can be decreased to 292 Hz for a predetermined amount of time.

The pulse rate of the second plurality of red LEDs 16 and the third plurality of infrared LEDs 18 can be increased to 438 Hz for a predetermined amount of time.

The pulse rate of the second plurality of red LEDs 16 and the third plurality of infrared LEDs 18 can be increased to 730 Hz for a predetermined amount of time.

The pulse rate of the second plurality of red LEDs 16 and the third plurality of infrared LEDs 18 can be increased to 1168 Hz for a predetermined amount of time.

The pulse rate of the second plurality of red LEDs 16 and the third plurality of infrared LEDs 18 can be increased to 1893 Hz for a predetermined amount of time.

The pulse rate of the second plurality of red LEDs 16 and the third plurality of infrared LEDs 18 can be increased to 2958 Hz for a predetermined amount of time.

The pulse rate of the second plurality of red LEDs 16 and the third plurality of infrared LEDs 18 can be increased to 4950 Hz for a predetermined amount of time.

The pulse rate of the second plurality of red LEDs 16 and the third plurality of infrared LEDs 18 can be decreased to 586 Hz for a predetermined amount of time.

The pulse rate of the second plurality of red LEDs 16 and the third plurality of infrared LEDs 18 can be increased to 880 Hz for a predetermined amount of time.

The pulse rate of the second plurality of red LEDs 16 and the third plurality of infrared LEDs 18 can be increased to 1470 Hz for a predetermined amount of time.

The pulse rate of the second plurality of red LEDs 16 and the third plurality of infrared LEDs 18 can be increased to 2347 Hz for a predetermined amount of time.

The pulse rate of the second plurality of red LEDs 16 and the third plurality of infrared LEDs 18 can be increased to 3816 Hz for a predetermined amount of time.

The pulse rate of the second plurality of red LEDs 16 and the third plurality of infrared LEDs 18 can be increased to 6172 Hz for a predetermined amount of time.

The pulse rate of the second plurality of red LEDs 16 and the third plurality of infrared LEDs 18 can be increased to 9950 Hz for a predetermined amount of time.

The pulse rate of the second plurality of red LEDs 16 and the third plurality of infrared LEDs 18 can be decreased to 1146 Hz for a predetermined amount of time.

The pulse rate of the second plurality of red LEDs 16 and the third plurality of infrared LEDs 18 can be increased to 1760 Hz for a predetermined amount of time.

The pulse rate of the second plurality of red LEDs 16 and the third plurality of infrared LEDs 18 can be increased to 2941 Hz for a predetermined amount of time.

The pulse rate of the second plurality of red LEDs 16 and the third plurality of infrared LEDs 18 can be increased to 4716 Hz for a predetermined amount of time.

The pulse rate of the second plurality of red LEDs 16 and the third plurality of infrared LEDs 18 can be increased to 7692 Hz for a predetermined amount of time.

The pulse rate of the second plurality of red LEDs 16 and the third plurality of infrared LEDs 18 can be increased to 12345 Hz for a predetermined amount of time.

The first plurality of blue LEDs 14, the second plurality of red LEDs 16, and the third plurality of infrared LEDs 18 can have a duty cycle of 40%.

It will be understood that it would be unduly repetitious and obfuscating to describe and illustrate every reordering, combination and subcombination of the elements and the aspects described. Accordingly, all elements, processes, and subprocesses can be combined in any way and/or combination, and the present specification, including the drawings, shall be construed to constitute a complete written description of all reorderings, combinations and subcombinations of the elements, processes, and subprocesses and of the aspects described herein, and of the manner and process of making and using the elements, and shall support claims to any such combination or subcombination.

An equivalent substitution of two or more elements can be made for any one of the elements in the claims below or that a single element can be substituted for two or more elements in a claim. Although elements can be described above as acting in certain combinations and even initially claimed as such, it is to be expressly understood that one or more elements from a claimed combination can in some cases be excised from the combination and that the claimed combination can be directed to a subcombination or variation of a subcombination.

The foregoing disclosure provides illustration and description but is not intended to be exhaustive or to limit the implementations to the precise form disclosed. Modifications may be made in light of the above disclosure or may be acquired from practice of the implementations. As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein. As used herein, satisfying a threshold may, depending on the context, refer to a value being greater than the threshold, greater than or equal to the threshold, less than the threshold, less than or equal to the threshold, equal to the threshold, and/or the like, depending on the context. Although particular combinations of features are recited in the claims and/or disclosed in the specification, these combinations are not intended to limit the disclosure of various implementations. In fact, many of these features may be combined in ways not specifically recited in the claims and/or disclosed in the specification.

Although each dependent claim listed below may directly depend on only one claim, the disclosure of various implementations includes each dependent claim in combination with every other claim in the claim set. No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having" or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A photobiomodulation therapy device, comprising:

a receiving pad that is constructed to receive a portion of a user's body;

a first plurality of blue light emitting diodes (LEDs), wherein at least a first portion of the first plurality of blue LEDs is attached to the receiving pad;

a second plurality of red LEDs, wherein at least a first portion of the second plurality of red LEDs is attached to the receiving pad; and a third plurality of infrared LEDs, wherein at least a first portion of the third plurality of infrared LEDs is attached to the receiving pad;

a control circuitry operably coupled to the first plurality of blue LEDs, the second plurality of red LEDs, and the third plurality of infrared LEDs, wherein the control circuitry is configured to perform one of:

activate the first plurality of blue LEDs at so that the first plurality of blue LEDs each have a pulse rate of 146 Hz;

stepwise increase the pulse rate of the first plurality of blue LEDs from 146 Hz to 946 Hz;

deactivate the first plurality of blue LEDs;

activate the second plurality of red LEDs and the third plurality of infrared LEDs at so that the second plurality of red LEDs and the third plurality of infrared LEDs each have a pulse rate of 146 Hz;

stepwise increase the pulse rate of the second plurality of red LEDs and the third plurality of infrared LEDs from 146 Hz to 2487 Hz;

decrease the pulse rate of the second plurality of red LEDs and the third plurality of infrared LEDs from 2487 Hz to 292 Hz;

stepwise increase the pulse rate of the second plurality of red LEDs and the third plurality of infrared LEDs from 292 Hz to 4950 Hz;

decrease the pulse rate of the second plurality of red LEDs and the third plurality of infrared LEDs from 4950 Hz to 586 Hz;

stepwise increase the pulse rate of the second plurality of red LEDs and the third plurality of infrared LEDs from 586 Hz to 9950 Hz;

decrease the pulse rate of the second plurality of red LEDs and the third plurality of infrared LEDs from 9950 Hz to 1146 Hz; and stepwise increase the pulse rate of the second plurality of red LEDs and the third plurality of infrared LEDs from 1146 Hz to 12345 Hz;

wherein the red LEDs and the infrared LEDs are controlled using a non-monotonic pulse sequence including at least decrease in the pulse rate followed by a subsequent increase in the pulse rate for providing a light therapy to the user, wherein the non-monotonic pulse sequence includes a first peak pulse rate, a first valley pulse rate below the first peak pulse rate, a second peak pulse rate reached after the first valley pulse rate and greater than the first peak pulse rate, a second valley pulse rate below the second peak pulse rate and greater than the first valley pulse rate, and a third peak pulse rate reached after the second valley pulse rate and greater than the second peak pulse rate.

2. The photobiomodulation therapy device of claim 1, further comprising:

a base plate positioned below the receiving pad, wherein the receiving pad includes a first portion of the first plurality of blue LEDs, a first portion of the second plurality of red LEDs, a first portion of the third plurality of infrared LEDs;

a first arm pivotally connected to the base plate, wherein the first arm includes a second receiving pad with a second portion of the blue LEDs, a second portion of the second plurality of red LEDs, and a second portion of the third plurality of infrared LEDs; and a second arm pivotally connected to the base plate, wherein the second arm includes a third receiving pad with a third portion of the blue LEDs, a third portion of the red LEDs, and a third portion of the infrared LEDs, further wherein the base plate is positioned between the first arm and the second arm, further wherein the control circuitry controls of the first plurality of blue LEDs, the second plurality of red LEDs and the third plurality of infrared LEDs attached with the first arm and the second arm.

3. The photobiomodulation therapy device of claim 2, wherein: the control circuitry performs one of:

activate the second portion of the first plurality of blue LEDs each have the pulse rate of 146 Hz;

stepwise increasing the pulse rate of the second portion of the first plurality of blue LEDs from 146 Hz to 946 Hz;

deactivate the second portion of the first plurality of blue LEDs; and activate the second portion of the second plurality of red LEDs and the third portion of the second plurality of red LEDs, the second portion of the third plurality of infrared LEDs and the third portion of the third plurality of infrared LEDs each have the pulse rate at 146 Hz; and stepwise increasing the pulse rate of the second portion of the second plurality of red LEDs, the third portion of the second plurality of red LEDs, a second portion of the third plurality of infrared LEDs and the third portion of the third plurality of infrared LEDs from 146 Hz to 12345 Hz, wherein the red LEDs and the infrared LEDs are controlled using a non-monotonic pulse sequence including at least decrease in the pulse rate followed by a subsequent increase in the pulse rate.

4. The photobiomodulation therapy device of claim 1, further comprising: a portable battery positioned on the receiving pad and directly connected with the first plurality of blue LEDs, the second plurality of red LEDs, and the third plurality of infrared LEDs to provide power.

5. The photobiomodulation therapy device of claim 1, further comprising: a sensor for providing a sensor data to control the pulse rate of at least one of the first plurality of blue LEDs, the second plurality of red LEDs, and the third plurality of infrared LEDs.

6. A photobiomodulation therapy device, comprising:

a first receiving pad that is constructed to receive a first portion of a user's body;

a second receiving pad that is constructed to receive a second portion of the user's body;

a first plurality of blue light emitting diodes (LEDs), wherein at least a first portion of the first plurality of blue LEDs is attached to the first receiving pad, and wherein at least a second portion of the first plurality of blue LEDs is attached to the second receiving pad;

a second plurality of red LEDs, wherein at least a first portion of the second plurality of red LEDs is attached to the first receiving pad, and wherein at least a second portion of the second plurality of red LEDs is attached to the second receiving pad; and a third plurality of infrared LEDs, wherein at least a first portion of the third plurality of infrared LEDs is attached to the first receiving pad, and wherein at least a second portion of the third plurality of infrared LEDs is attached to the second receiving pad;

a control circuitry operably coupled to the first plurality of blue LEDs, the second plurality of red LEDs, and the third plurality of infrared LEDs, wherein the control circuitry is configured to perform one of:

activate the first plurality of blue LEDs so that the first plurality of blue LEDs each have a pulse rate of 146 Hz;

stepwise increase the pulse rate of the first plurality of blue LEDs from 146 Hz to 946 Hz;

deactivate the first plurality of blue LEDs;

activate the second plurality of red LEDs and the third plurality of infrared LEDs so that the second plurality of red LEDs and the third plurality of infrared LEDs each have a pulse rate of 146 Hz;

stepwise increase the pulse rate of the second plurality of red LEDs and the third plurality of infrared LEDs from 146 Hz to 2487 Hz;

decrease the pulse rate of the second plurality of red LEDs and the third plurality of infrared LEDs from 2487 Hz to 292 Hz;

stepwise increase the pulse rate of the second plurality of red LEDs and the third plurality of infrared LEDs from 292 Hz to 4950 Hz;

decrease the pulse rate of the second plurality of red LEDs and the third plurality of infrared LEDs from 4950 Hz to 586 Hz;

stepwise increase the pulse rate of the second plurality of red LEDs and the third plurality of infrared LEDs from 586 Hz to 9950 Hz;

decrease the pulse rate of the second plurality of red LEDs and the third plurality of infrared LEDs from 9950 Hz to 1146 Hz; and stepwise increase the pulse rate of the second plurality of red LEDs and the third plurality of infrared LEDs from 1146 Hz to 12345 Hz;

wherein the red LEDs and the infrared LEDs are controlled using a non-monotonic pulse sequence including at least decrease in the pulse rate followed by a subsequent increase in the pulse rate for providing a light therapy to the user, wherein the non-monotonic pulse sequence includes a first peak pulse rate, a first valley pulse rate below the first peak pulse rate, a second peak pulse rate reached after the first valley pulse rate and greater than the first peak pulse rate, a second valley pulse rate below the second peak pulse rate and greater than the first valley pulse rate, and a third peak pulse rate reached after the second valley pulse rate and greater than the second peak pulse rate.

7. The photobiomodulation therapy device of claim 6, further comprising:

a base plate positioned below the first receiving pad, wherein the first receiving pad includes a first portion of the first plurality of blue LEDs, a first portion of the second plurality of red LEDs, a first portion of the third plurality of infrared LEDs;

wherein the first arm includes the second receiving pad with a second portion of the blue LEDs, a second portion of the second plurality of red LEDs, and a second portion of the third plurality of infrared LEDs; and a second arm pivotally connected to the base plate, wherein the second arm includes a third receiving pad with a third portion of the blue LEDs, a third portion of the red LEDs, and a third portion of the infrared LEDs, further wherein the base plate is positioned between the first arm and the second arm, further wherein the control circuitry controls of the first plurality of blue LEDs, the second plurality of red LEDs and the third plurality of infrared LEDs attached with the first arm and the second arm, wherein the first receiving pad is disposed on the base plate and positioned between the first arm and second arm.

8. The photobiomodulation therapy device of claim 7, wherein: the control circuitry performs one of:

activate the second portion of the first plurality of blue LEDs each have the pulse rate of 146 Hz;

stepwise increasing the pulse rate of the second portion of the first plurality of blue LEDs from 146 Hz to 946 Hz;

deactivate the second portion of the first plurality of blue LEDs; and activate the second portion of the second plurality of red LEDs and the third portion of the second plurality of red LEDs, the second portion of the third plurality of infrared LEDs and the third portion of the third plurality of infrared LEDs each have the pulse rate at 146 Hz; and stepwise increasing the pulse rate of the second portion of the second plurality of red LEDs, the third portion of the second plurality of red LEDs, a second portion of the third plurality of infrared LEDs and the third portion of the third plurality of infrared LEDs from 146 Hz to 12345 Hz, wherein the red LEDs and the infrared LEDs are controlled using a non-monotonic pulse sequence including at least decrease in the pulse rate followed by a subsequent increase in the pulse rate.

9. The photobiomodulation therapy device of claim 6, further comprising: a portable battery positioned on the first receiving pad and directly connected with the first plurality of blue LEDs, the second plurality of red LEDs, and the third plurality of infrared LEDs to provide power.

10. A photobiomodulation therapy device, comprising:

a receiving pad that is constructed to receive a portion of a user's body;

a first plurality of blue light emitting diodes (LEDs), wherein at least a first portion of the first plurality of blue LEDs is attached to the receiving pad;

a second plurality of red LEDs, wherein at least a first portion of the second plurality of red LEDs is attached to the receiving pad; and a third plurality of infrared LEDs, wherein at least a first portion of the third plurality of infrared LEDs is attached to the receiving pad;

a control circuitry operably coupled to the first plurality of blue LEDs, the second plurality of red LEDs, and the third plurality of infrared LEDs, wherein the control circuitry is configured to perform one of:

activate the first plurality of blue LEDs so that the first plurality of blue LEDs each have a pulse rate of 146 Hz;

stepwise increase the pulse rate of the first plurality of blue LEDs from 146 Hz to 946 Hz;

deactivate the first plurality of blue LEDs;

activate the second plurality of red LEDs and the third plurality of infrared LEDs so that the second plurality of red LEDs and the third plurality of infrared LEDs each have a pulse rate of 146 Hz;

increase the pulse rate of the second plurality of red LEDs and the third plurality of infrared LEDs from 146 Hz to 2487 Hz;

decrease the pulse rate of the second plurality of red LEDs and the third plurality of infrared LEDs from 2487 Hz to 292 Hz;

increase the pulse rate of the second plurality of red LEDs and the third plurality of infrared LEDs from 292 Hz to 4950 Hz;

decrease the pulse rate of the second plurality of red LEDs and the third plurality of infrared LEDs from 4950 Hz to 586 Hz;

increase the pulse rate of the second plurality of red LEDs and the third plurality of infrared LEDs from 586 Hz to 9950 Hz;

decrease the pulse rate of the second plurality of red LEDs and the third plurality of infrared LEDs from 9950 Hz to 1146 Hz; and increase the pulse rate of the second plurality of red LEDs and the third plurality of infrared LEDs from 1146 Hz to 12345 Hz;

wherein the red LEDs and the infrared LEDs are controlled using a non-monotonic pulse sequence including at least decrease in the pulse rate followed by a subsequent increase in the pulse rate for providing a light therapy to the user, wherein the non-monotonic pulse sequence includes a first peak pulse rate, a first valley pulse rate below the first peak pulse rate, a second peak pulse rate reached after the first valley pulse rate and greater than the first peak pulse rate, a second valley pulse rate below the second peak pulse rate and greater than the first valley pulse rate, and a third peak pulse rate reached after the second valley pulse rate and greater than the second peak pulse rate.

* * * * *